United States Patent [19]

Ludwig et al.

[11] Patent Number: 4,784,952

[45] Date of Patent: Nov. 15, 1988

[54] CONFERRED SUSCEPTIBILITY TO LAMBDA PHAGE IN NON-COLIFORM PROCARYOTIC HOSTS

[75] Inventors: Robert A. Ludwig, Santa Cruz, Calif.; Gert E. de Vries, Leiden, Netherlands

[73] Assignee: The Regents of the University of California, Berkeley, Calif.

[21] Appl. No.: 715,124

[22] Filed: Mar. 21, 1985

Related U.S. Application Data

[63] Continuation-in-part of Ser. No. 656,693, Oct. 1, 1984, abandoned.

[51] Int. Cl.[4] ............... C12P 19/34; C12N 15/00; C12N 1/20; C07H 15/12
[52] U.S. Cl. ................. 435/91; 435/172.1; 435/172.3; 435/253; 435/320; 536/27; 935/29; 935/41
[58] Field of Search ............... 435/68, 172.3, 317, 435/91; 935/26, 27, 29, 72; 536/27

[56] References Cited

PUBLICATIONS

Clement et al., Cell, 27(2), 507–514, 1981 (Dec.).
De Vries et al., 1984, "Extension of Bacteriophage α Host Range: Selection, Cloning, and Characterization . . .", Proc. Natl. Acad. Sci., vol. 81, 6080–6084.
Harkki et al., 1984, "Application of Phage λ Technology to Salmonella Typhimurium", Mol. Gen. Genet., vol. 95, 256–259.
Palva et al., 1981, "Cosmid Cloning and Transposon Mutagenesis in Salmonella Typhimurium", Mol. Gen. Genet., vol. 181, 153–157.
Bailey et al., 1974, Diagnostic Microbiology, 4th Ed., C. V. Mosby Co., St. Louis, p. 65.
Friedman et al., 1982, "Construction of a Broad Host Range Cosmid Cloning Vector . . . ", Gene, vol. 18, 289–296.
Schell et al., 1983, "The Ti Plasmids as Natural and as Practical Gene Vectors for Plants", BioTechnology, Apr. 1983, pp. 175–180.

Primary Examiner—Thomas G. Wiseman
Assistant Examiner—Thomas D. Mays
Attorney, Agent, or Firm—Ciotti & Murashige, Irell & Manella

[57] ABSTRACT

Vectors suitable for effecting expression of lamB protein in a desired procaryotic host, and methods for their construction, are disclosed. Transformation with these vectors results in the ability of the procaryotic host to sustain infection by lambda phage.

18 Claims, 2 Drawing Sheets

CONFERRED SUSCEPTIBILITY TO LAMBDA PHAGE IN NON-COLIFORM PROCARYOTIC HOSTS

REFERENCE TO GOVERNMENT SUPPORT

This invention was made with Government support under Grant No.: PCM 8021591 with the National Science Foundation and Grant No.: 80-CRCR-1-0470 with the United States Department of Agriculture and the University of California. The Government has certain rights in this invention.

CROSS-REFERENCE TO A RELATED APPLICATION

This is a continuation-in-part of U.S. Ser. No. 656,693, filed Oct. 1, 1984, now abandoned.

DESCRIPTION

1. Technical Field

This invention relates to the field of modification of organisms by recombinant technology. More specifically, it relates to vectors and procedures useful in conferring susceptibility to lambda phage on non-coliform host cells.

2. Background Art

Recombinant DNA manipulations involving sequences packaged into lambda phage has become a routinely used and extremely important tool in obtaining, modifying, and replicating desired DNA sequences. For example, the entire set of sequences available from a desired species source can be inserted into lambda phage and reproduced in quantity. Even organisms having complex genomes such as human beings have yielded complete genomic banks through the intermediation of the lambda phage technique.

Another significant contribution of the lambda phage system is that it offers the possibility of both random and site-directed tranposon mutagenesis. For random transposon mutagenesis, lambda phage carrying a wide variety of transposons have been constructed. Bacteria susceptible to lambda can be infected with as many as 100 lambda, transposon-containing DNA molecules. Although transposition is very infrequent, because the number of transposon mutants eventually obtained is proportional to the number of transposon elements in a given cell that are available for transposition, the presence within the cell of this large number of transposon elements increases the frequency of mutation. It therefore becomes feasible to obtain a library of random transposon mutants within each and every gene of the host cell.

For site-directed transposon mutagenesis identified recombinant DNA clones contained in a lambda DNA vector can be mutagenized and the mutant site physically mapped in *E. coli*. These mutated recombinant clones can be packaged into defective viral particles in *E. coli*, in vivo and subsequently used to infect cells from which DNA for the recombinant clones were derived and now made susceptible to lambda. Because lambda cannot replicate in these cells, the mutant genes can only survive and be propagated if they recombine (homologously) into the genomes of these cells.

While the sequences packed into phage can originate from any source, the host cell utilized to infect and replicate the phage is presently limited to several *E. coli* serotypes. The result of this limitation is that phage infection cannot be used as a mechanism for transformation in any other cell, nor can the replication environment of any other cell type be utilized. There are instances in which it is clearly advantageous to enable the phage mechanism to be used in alternative hosts.

For example, certain non-coliform bacteria, specifically strains of Agrobacterium, are effective in transforming the cells of higher plants. Because the transformation or conjugal DNA transfer efficiency of non-infective DNA—e.g., plasmid DNA, is so low, it is necessary to construct the appropriate Agrobacterium, by transforming with relatively large amounts of a homogeneous DNA preparation containing the desired sequences. Thus, for example, in order to provide a targeted host plant with resistance to a particular insect or to a pesticide by causing it to manufacture a resistance-conferring enzyme, the gene encoding that enzyme must be cloned and, thus amplified, ligated to host compatible control sequences and transformed into the Agrobacterium infective vector which is then used to infect the plant. These manipulations of the transforming DNA are necessary because only approximately 1 in $10^6$ molecules of available DNA will successfully enter the host.

Lambda phage infection, on the other hand, provides nearly 100% DNA transfer efficiency into the cell—i.e., virtually all of the available DNA molecules which are packed into phage succeed in entering the cells. Taking advantage of this efficiency, it will be possible to transduce an Agrobacterium host with the entire genomic library from a donor plant that is resistant to an insect or pesticide (due to the production of the resistance conferring enzyme) without manipulations to segregate the gene of interest since the entire population of DNA sequences including that of the desired gene will be transformed into the bacterial host. It is then necessary only to select the subsequently infected plants for the desired property.

That current DNA transfer efficiencies do not permit transfer of recombinant clones to their indigenous cells is clear from consideration of the number of coding sequences available in an entire genome. Current estimates are that there are, in any restriction digest of higher eucaryote genomic DNA, approximately $10^8$ candidate DNA fragments only two or three of which contain the desired gene sequence. Using presently known transformation techniques operating at an efficiency of $10^{-6}$ DNA$^{-1}$, 1000 cells would be required to obtain one transformant containing any one of the $10^8$ fragments; at least $10^{11}$ cells would be required to obtain a complete library. On the other hand, using lambda phage, at least 1 in $10^8$ in vivo packaged phage should contain a recombinant DNA clone, and target cells could be quantitatively infected. Thus, an entire genomic library of a higher eucaryote could be obtained in, at most, $10^8$ lambda-susceptible cells.

In short, the enhanced DNA transfer efficiency available through infection by lambda phage would permit omission of intervening genetic manipulation steps in securing genetic transfer between species. It would also greatly enhance the versatility, in general, of host use for expression of desired gene sequences without requiring such intermediate gene manipulation steps.

*E. coli* are uniquely capable of supporting infection by lambda phage because only *E. coli* construct suitable outer membrane proteins, designated lamB proteins, which act as receptors for the phage. A good deal is known about these receptors. First, the lamB protein is a major constituent of the outer membrane in *E. coli*. (See, for example, Hall, M. N., et al, *Annual Rev Genet* (1981) 15:91.) The lamB protein is encoded in the MalB region of the *E. coli* chromosome (Reibaud, O., et al, *Mol Gen Genet* (1979) 1974:241), which is part of the maltose regulon. Presumably this location is logical because lamB protein normally participates in the transport of maltose and maltodextrins, which transport is required for these saccharides to be used as carbon sources, across the outer membrane. As the lamB coding sequence is under the control of a promoter associated with maltose uptake, it is not surprising that the production of lamB is inducible under conditions of high maltose concentration, and repressible in the presence of glucose, the product of maltose degradation. Indeed, it is also known that the pertinent promoter is regulated by the malT protein, another gene product of the maltose operon.

The coding sequence for lamB would be expressible in other organisms, thereby conferring lambda phage susceptibility on them, if it were removed from its *E. coli*-specific expression system and placed into operable linkage with control sequences compatible with such other organisms. Presumably the encoded signal sequence ordinarily associated with lamB would be successful in transporting the product of the expressed gene to the hosts' outer membrane because another *E. coli* signal, the β-lactamase signal sequence, has been shown to be virtually universal in its capability of transporting proteins through membranes, both in procaryotic and eucaryotic cells, (Talmadge, K., et al, *Proc Natl Acad Sci* (USA) (1980) 77:3369 and Talmadge, K., et al, *Proc Natl Acad Sci* (USA) (1980) 77:3988). Thus the expression of the lamB protein along with its native signal sequence will result in formation of membrane proteins in non-coliform species, in particular, in such Gram-negative species as Agrobacterium which is peculiarly useful for plant transformation.

Disclosure of the Invention

The invention provides vectors and methods which are useful in conferring lambda phage susceptibility on a wide range of non-coliform cells. The vectors and methods so provided permit the versatility of lambda phage based recombinant DNA techniques to be performed in other Gram-negative bacteria, as well as in eucaryotic cells such as yeast and mammalian cells. This is of special significance because of the ability of certain non-coliform strains of Gram-negative procaryotes species to infect and transform higher plant hosts.

Thus, in one aspect, the invention relates to expression vectors effective in conferring susceptibility to lambda phage infection in non-coliform cells. These vectors contain promoter and other pertinent control sequences compatible with such cells suitably and operably linked to the coding sequence for the lamB protein and its signal. They also contain some mechanism for replication, such as a compatible origin of self replication or sufficient homology for chromosome integration into the host.

In other aspects, the invention includes precursor vectors to the above plasmids which comprise a suitable replication region, along with the coding region for lamB and its signal. Recombinant cells transformed with the foregoing vectors are also included in the invention.

Other aspects of the invention include a method for producing cells receptive to lambda phage infection, a method for transforming non-coliform cells at high efficiency using lambda phage as vector, and methods for obtaining the lambda phage susceptibility conferring plasmids. The invention in other aspects relates to a method for transforming higher plants using lambda phage transformed cells, and to the plants so transformed.

MODES OF CARRYING OUT THE INVENTION

A. Definitions

Figure 1:
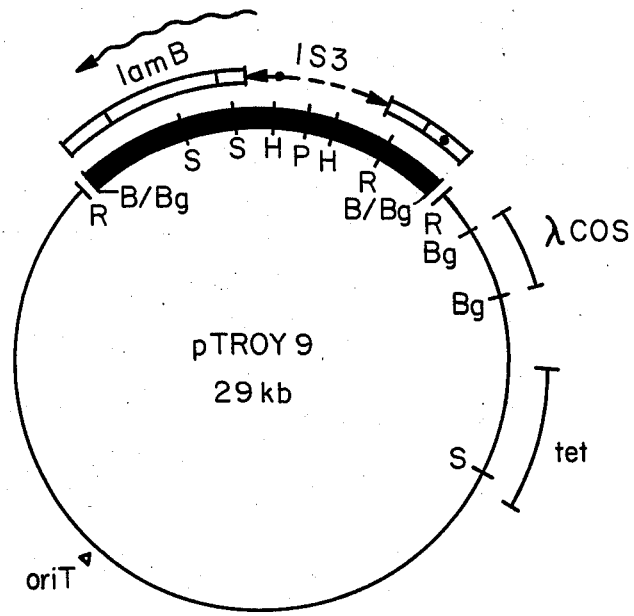
FIG. 1 is a diagram of the precursor plasmid, pTROY9 showing the inserts and restriction sites.
Figure 2:
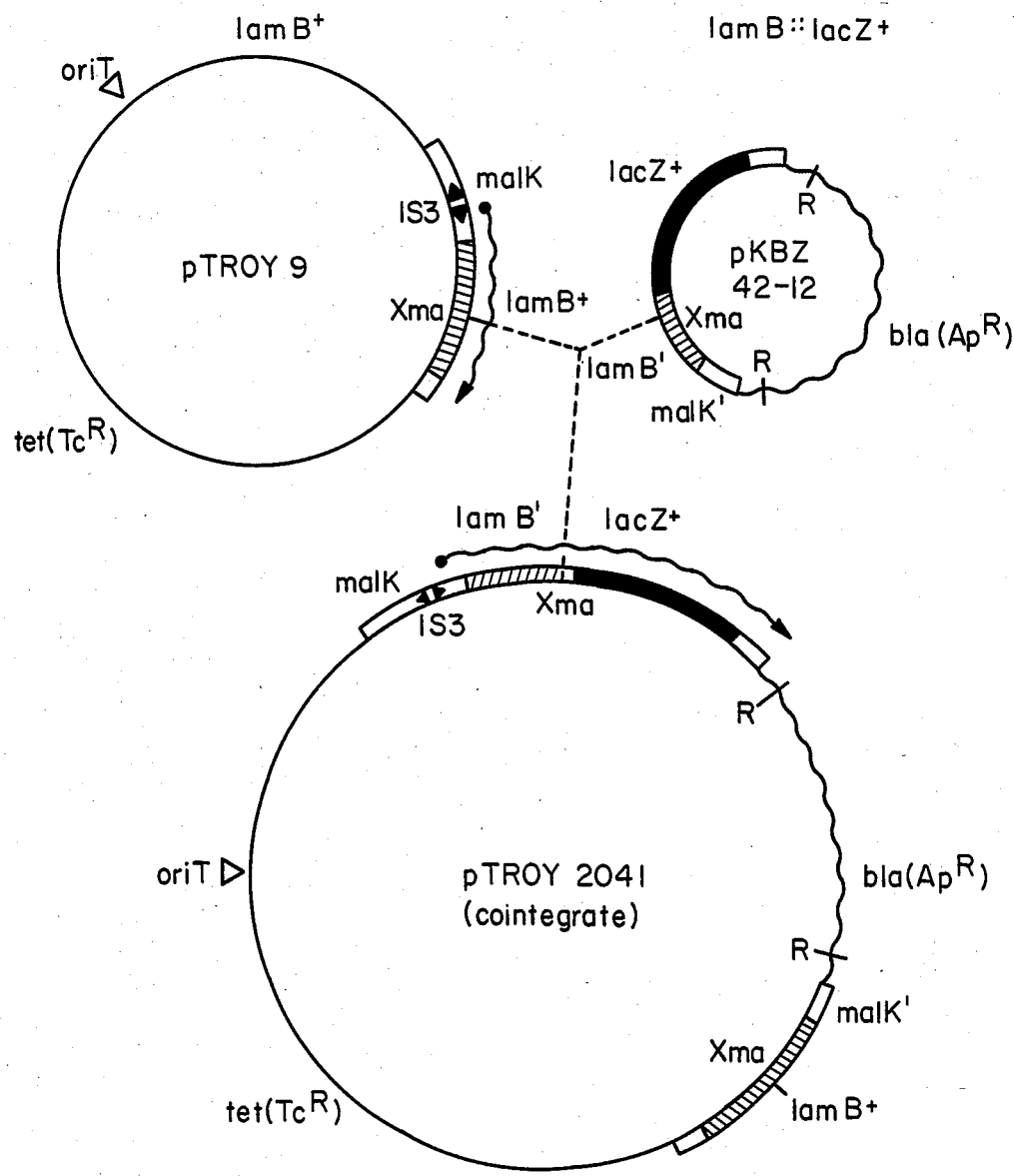
FIG. 2 diagrams the cointegrate pTROY2041 which results from recombination of pTROY9 with pKBZ42-12.

As used herein, "lamB protein" refers to the receptor protein responsible for binding lambda phage to the outer membrane of *E. coli*. The amino acid sequence of this protein is disclosed in Clement, J. M., et al, *Cell* (1981) 27:507–514. Amino acid sequences which contain minor modifications of this published sequence which do not destroy functionality are included in the definition, as it is understood that limited natural variability of peptide sequences is commonplace.

LamB, as found in the *E. coli* outer membrane is a 421 amino acid sequence. When produced in the cytoplasm, it also contains a signal sequence which is, of course, lost when the mature protein is transported across the inner membrane and into the periplasmic space. "LamB" or "LamB protein" includes both the mature protein and the form containing leader unless otherwise clear from the context.

"Recombinant lamB protein" refers to lamB which is produced under the control of other than its normally associated control sequences. Such control sequences are present only in *E. coli*, and include the promoter/operator which is maltose incducible and glucose repressible.

"Appropriate" or "compatible" control sequences refer to those DNA sequences which are required to effect the expression of operably linked coding sequences in the host referred to. Such control sequences include promoter sequences in all species, and, in procaryotes, ribosome binding sites, in eucaryotes, termination signals, and may further include additional elements whose nature is not, at present, understood.

"Operably linked" refers to juxtaposition such that the normal function of the components can be realized. Thus, a promoter "operably linked" to a coding sequence is in such a configuration that the coding sequence can be expressed under the control of this promoter.

"Non-coliform" host cells refers to those host cells which are normally not susceptible to infection by lambda phage. Lambda phage presently and natively infect only various species of *Escherichia coli*, and not other unrelated bacteria.

Transformed or recombinant "cells" refer to cells which contain additional genetic material through manipulation involving transformation, transduction, conjugation or other such techniques for introduction of DNA. "Cells" includes harvested cells and cell cultures, and, of course, the progeny of the original transformed or recombinant DNA recipient cell.

B. General Description

The vectors and methods of the invention were developed according to a strategy comprising controlled selection, plasmid recombination, and bacterial conjugation. This approach is illustrative, and its description here does not imply that the vectors and cells of the invention could not be produced by other means. The desired product is a vector capable of effecting the expression of lamB in a selected desired host, or, in the alternative, cells of that host which have been genetically modified so that lamB protein is produced. In the description below, both the vector and the modified host cells are obtained from a precursor vector which contains the coding sequence for lamB and a replication means operable in the host. A short summary of the rationale and strategy is as follows:

The expression of lamB was first made constitutive in *E. coli*, thereby providing a promoter that could be more simply modified to give wide host range compatibility. The modified promoter/coding sequence fragment was placed in a broad (procaryotic) host range vector to give the aforementioned "precursor". The precursor was, indeed, the end product in the case of bacteria closely related to *E. coli*, which were then able to replicate the vector and express lamB. The precursor was also, however, modified by selective recombination with a selectable fusion flag containing vector to obtain operably linked promoters compatible with a still broader range of hosts. By appropriate selection of the fusion flag, the control sequence can be adapted to any procaryotic or eucaryotic host.

The expression of the lamB sequence was removed from the control of the regulatable promoter native to its usual circumstances by selecting strains of *E. coli* for which expression of the lamB protein was constitutive. The selection was made in two stages: First, a phage lambda resistant ($\lambda^R$) strain of *E. coli*, ECG1, was selected. ECG1, though resistant at low phage levels, could still absorb lambda packaged DNA to a limited extent. This was shown by acquisition by ECG1 of tetracycline resistance ($Tc^R$) when high concentrations of lambda packaged $Tc^R$ gene were used. The relatively low level of lamb produced was evidently due to a mutant form of the malT protein fragment. (The malT is normally required to stimulate the promoter.)

ECG1 thus provided a population of candidates for constitutive lamB production —i.e., some of these selected malT− cultures are expected to revert to high levels of lamB production by alteration of the promoter so as not to require presence of malT protein. These naturally occurring mutations were then selected for by growing the cells in the presence of tetracycline and providing the transposon Tn5-132 (Berg, D. E., et al, *Cold Spring Harbor Quant Biol* (1981) 45:115) packaged in lambda phage. The Tn5-132 sequence confers tetracycline resistance. Therefore, cells that produce more lamB protein and are thus capable of greater uptake of the Tn5-132 containing phage were selected from those with successful growth in the presence of tetracycline. The existence of these successful colonies showed the promoter no longer required malT.

Having obtained expression of the lamB sequence under the control of a suitable promoter (which turned out to be the IS3 promoter, associated with a known "jumping gene") the promoter/coding sequence fragment was obtained from the selected (ECG10) derivative chromosome by digestion with BglII, a restriction enzyme chosen by analogy to the procedure for obtaining the lamB operon from wild type cells. (Clement, J. M., et al, *Cell* (1981) 27:507; Bedouelle, H., et al, *Mol Gen Genet* (1982) 185:82; Clement, J. M., *Mol Gen Genet* (1982) 185:82.)

The isolated fragment containing the coding sequence under the control of the IS3 promoter was cloned into the BamHI site of the broad host range, restricted copy number cosmid pLAFRB derived from pLAFR1 (Friedman, A. M., et al, *Gene* (1982) 18:289) which contains, in addition to its broad host range origin of replication, the tetracycline resistance marker, and OriT, a sequence which binds to the base of pilus protein in *E. coli* and facilitates conjugative transfer of the plasmid DNA. The resulting plasmid, pTROY9 (see FIG. 1) is thus capable of replicating in a broad range of hosts, of conferring tetracycline resistance, and of transferring the lamB protein encoding sequence along with IS3 promoter and the remainder of the plasmid into targeted receptor cells.

pTROY9 was, upon such transfer, itself successful in conferring the ability to produce lamB protein constitutively on closely related bacterial hosts such as *Klebsiella pneumoniae*, and *Salmonella typhimurium*.

pTROY9, however, was not successful in producing lamB protein in strains which were more distantly related to the coliform donors and, with respect to these, must be regarded as a precursor plasmid. This is significant, especially, since some of these strains such as Agrobacterium and Rhizobium are potentially among the most useful when transformed with these sequences. The following approach was used to place the lamB sequences under the control of promoters other than or derived from IS3, which was evidently not functional in these more distantly related hosts.

Controlled selection was made for specific colonies where the targeted host rearranged the plasmid DNA so that more appropriate control sequences were placed into operable linkage with the lamB codons. To accomplish this, the desired hosts were cotransformed with pTROY9 and a vector containing a portion of the lamB sequences in reading frame with the lacZ sequence as a fusion flag. The fusion (lamB::lacZ) was supplied by pKBZ42-12 (a narrow host range (colE1 replicon) vector containing no defined promoter operably linked to the sequences, but conferring ampicillin resistance ($Amp^R$) on cells harboring it. This vector was obtained from Benson, S. and Silhavy, T., Frederick Cancer Research Facility, Frederick, MD (Benson, S., et al, *Cell* (1983) 32:1325).

The cotransformed cells were then selected for recombinants between plasmids pTROY9 and pKBZ42-12. The formation of the recombinant plasmids is facilitated by the homology of the lamB sequences in each. Successful recombinant plasmids, for example pTROY2041, illustrated below, contain a lamB::lacZ fusion where the IS3 promoter region is in operable linkage to the fusion. Since the desired host is a non-*E. coli* host, and the ColE1 origin of replication from pKBZ42-12 is unworkable in such hosts, only cells containing successful recombinant plasmids will be the $Amp^R$ or $LacZ^+$. By selection of only $Amp^R$ or $LacZ^+$ cells, the presence of the recombination plasmid is assured.

Selection of mutants which contain the IS3 promoter region (sufficiently modified) to express the lacZ::lamB fusion flag is provided by growing the $Amp^R$ (where selectable) colonies on lactose-containing medium. By virtue of this selection, colonies which constitutively express high levels of the lacZ fusion flag arise and can be screened using the color intensity of the β-galactosidase assay substrate IPTG on medium not containing lactose. When such colonies are found, the lactose selection is removed, permitting the recombinant plasmid to dissociate into the pKBZ42-12 component and a modified pTROY9, pTROY9'—a generic name for such modified plasmids. pTROY9' now contains a modification in the IS3 promoter permitting lamB expression in the host cell.

The resultant pTROY9' plasmid is then replicated, isolated and sequenced, or the transformed hosts are retained as cells capable of lamB expression.

pTROY9' represents a subclass of plasmids capable, as a group, of effecting the expression of lamB receptor protein in the entire range of host cell possibilities. The elements of its construction which permit it to effect this expression are the entire lamB coding sequence in operable linkage to a promoter, which is in turn operable in the procaryote of interest when coupled with a replicon that is functional in the procaroyte of interest. For convenience, it also carries a tetracycline resistance marker gene.

pTROY9' may be considered a specialized derivative of pTROY9 adapted for the procaryotic host of interest. pTROY9 is a generalized precursor which is capable of being converted to pTROY9' because of the following features: it contains a coding sequence for lamB operably linked to a promoter which allows its replication and expression in $E. coli$ and which is presumably closely enough related to the desired promoter to permit it to function as a substrate for mutation. It also contains a replicon operable in the procaryote of interest as well as the tetracycline marker. For convenience, in addition, it carries an oriT replicon which permits the DNA of this plasmid to be transferred by conjugation to any host. This replicon is particularly useful for transfer of pTROY9 into hosts which are closely enough related that pTROY9 itself may be used as an expression vector.

pTROY9 can also be prepared in modifications suitable for eucaryotic cells. A means of replication operable in such cells, such as an ARS region suitable for yeast, a viral replication origin or designed homology for host chromosome integration might be used. In addition, for convenience, a selectable marker analogous to the Tc$^R$ marker of pTROY9 could be included—for example, the DHFR or TK markers.

pTROY9 is converted to pTROY9' with the assistance of a vector carrying a selectable fusion flag to the lamB protein. For procaryotic systems, the lacZ fusion flag wherein the lacZ protein is appended to the carboxyl terminus of the lamB receptor protein, permits selection of cells which are capable of metabolizing lactose or lactose-analogs; i.e., it is possible to apply selection pressure for only those cells which are capable of producing the fusion flag. The effectiveness of this flag may be limited to cells constructing lactose permease which permits lactose or its analogs to enter the cell, although because the lamB::lacZ fusion is exported, the permease may be dispensable. Thus, the lacZ flag per se would be applicable to procaryotes and lower eucaryotes which can be made Lac$^-$ by mutation. Higher eucaryotic organisms generally do not produce this permease, and the lacZ flag is as yet not effective in such selections.

Thus, to modify the strategy set forth above to make it applicable to higher eucaryotic hosts, it is necessary only to provide a plasmid analogous to pKBZ42-12 which contains a fusion flag carrying a protein segment capable of conferring characteristics which are responsive to selection pressure on higher eucaryotes, or to introduce a lactose permease. Such proteins include herpes thymidine kinase or hypoxanthine-quanine phosphoribosyl transferase.

C. Utility of pTROY9'

Even for those pTROY9' plasmids which have been adapted only to other procaryotes the conferred ability to produce lamB protein represents an important enablement of practical significance. In general, all the manipulations which can be performed with the aid of lambda phage in $E. coli$ are enabled to be performed in any desired procaryotic cell. This means that any procaryotic host, not just $E. coli$, can be efficiently transformed with a multiplicity of coding sequences which can then be replicated and selected for use in the new procaryotic host. Furthermore these bacteria, in addition to $E. coli$, can now harbor genomic libraries of eucaryotic organisms constructed in broad host-range cosmid vectors. In an application of particular importance, Agrobacterium, which is known to transform plants, may thus acquire a complete genomic library of a plant with a particular desired characteristic, such as pesticide resistance, and then be used to infect a targeted host plant. As the pesticide characteristic can be selected for in the target host, and as the genomic sequences will be presumably carry with them control sequences which are operable in any higher plant, the desired characteristic can thus be directly transferred without the necessity of probing for the desired coding sequence, constructing specific expression vectors with known promoters and transforming the target plant with these especially constructed vectors.

For those embodiments of pTROY9' plasmids which carry adapted promoters to express the lamB sequence in eucaryotic host cells directly, the eucaryotes targeted will assume the same capability of efficient uptake for lambda packaged DNA now possessed by $E. coli$, and the process for expressing the sequences encoding eucaryotic peptides in analogous host cell lines will be streamlined accordingly. For example, in mammalian hosts, the expression of the coding sequences for growth hormones, lymphokines, interferons, enzymes, or of various growth factors can be obtained in a manner analogous to that described for transformation of plants. That is, the entire human genomic complement packaged into lambda phage may then be directly transformed into a desired eucaryotic host, such as a HeLa, CHO, VERO, or other available cell line, and the transformants selected for the production of the protein desired. The means for selection will, of course, vary with the protein desired to be produced, but by way of example, transformants which are producing the enzyme thymidine kinase, can be directly assayed for resistance to antifolate drugs. Any desired protein can, of course, be assayed by Western blot or immunoprecipitation of antibodies raised against it in a cellular extract.

This approach can also be used to modify the genetic complement of industrial organisms such as yeast to permit them to carry out enzymatic activities useful in the conversion of industrial substrates to desired products.

In sum, by providing a DNA transfer method which is 100% efficient, the acquisition of lamB susceptibility by a targeted host permits alteration of its genome by direct lambda-mediated infection with a mixture of genes known to contain the desired sequence and direct selection of the desired derivative strains, without the necessity of cloning and isolating the desired sequence and ligating it into specific expression vector constructions.

The capabilities conferred on hosts by pTROY9' plasmids also permits the extension of the "maxicell" technique beyond *E. coli*. In this technique, the protein encoded by a particular genomic sequence, such as an oncogene, and that ultimately produced by this sequence can be studied. While the amino acid sequence can be deduced from the coding sequence, definition of the correct start position is not always obvious and neither subsequent processing steps, nor results of catalytic activities of the encoded protein on other cellular components can be deduced directly. In the maxicell technique, the background genome of the cell, but not the processing machinery are destroyed by radiation, and the sequence to be studied is multiply introduced into the cell by lambda phage infection. Under these circumstances the sequence carried by the lambda phage is the only one available for transcription, translation and processing by the host. By using 35-S labeled methionine or other labeled amino acid, the resulting products can be identified and studied. Clearly the study of oncogene products, for example, in *E. coli* is not very useful; the study of oncogene products in typical transformed tumor cells is.

The following example is intended to illustrate, but not to limit the invention. It describes in detail the construction of the universal precursor vector pTROY9, and the conversion of pTROY9 into an adapted plasmid pTROY9' by recombination with a vector containing the lacZ fusion flag.

D.1. Techniques

D.1.a. Assay for LamB Receptor Protein Production

To assay for the production of lamB protein, cells were grown in minimal medium with either maltose or glucose as carbon source, harvested, washed with SM buffer, and diluted in SM buffer; 0.5 ml cell samples were mixed with 5 μl of $^3$H-labeled phage ($5.6 \times 10^{14}$ phage-$\mu$Ci$^{-1}$; 1 Ci=37 GBq) and incubated 30 min at 35° C. Cells and absorbed lambda particles were removed by centrifugation, and the unadsorbed phage in the supernatant counted by liquid scintillation. In the alternative, lamB activity was assayed by cosmid transduction.

D.1.b. Media

The media used in growth are as follows: LB medium (Davis, R. W., et al, *Advanced Bacterial Genetics* (1980) Cold Spring Harbor Laboratories, Cold Spring Harbor, New York); RM medium: R medium (Miller, J. H., *Experiments in Molecular Genetics* (1972) Cold Spring Harbor Laboratories, Cold Spring Harbor, N.Y. containing 10 mM MgSO$_4$/0.1% maltose; minimal medium: M9 salts with carbon sources supplied at 0.4%, amino acids at 0.01% and vitamins at 1 μg/ml.

D.2. Preparation of pTROY9

A phage resistant ($\lambda^R$) strain of *E. coli* derived from HB101, designated ECG1, was selected by growth of the HB101 parent strain on maltose deficient media, and screening for cultures capable of acquiring tetracycline resistance by transduction with the lambda phage packaged plasmid pN4 which contains the tetracycline resistance gene. ECG1 gave more than 500 colonies which were Tc$^R$ with an undiluted $\lambda^d$ (pN4) cosmid transducing lysate containing $5.7 \times 10^9$ lambda c1857/ml; successive ten fold dilutions gave only 440, 30 and 2 colonies respectively. Thus, high phage concentration was required for successful transduction, and, thus, lamB was shown to be produced only at low levels.

ECG1 was characterized by P1 transductional analysis and complementation tests to be mutant in the malT protein that induces the native lamB promoter.

Having thus obtained the production of lamB independent of control of the inducible system, revertants of ECG1 that were phage sensitive and that expressed lamB at a higher level were selected. To do this, ECG1 was infected with lambda::Tn5-132 which carries the tetracycline resistance conferring transposon Tn5-132 that transposes at relatively high frequency (about $10^{-4}$/infected cell). Thus, cells capable of adsorbing lambda phage at high levels have a greater chance of acquiring tetracycline resistance from Tn5-132. ECG1 was infected with lambda::Tn5-132 at a moi of 50 and was plated on LB+tetracycline (10 μg/ml). Tc$^R$ colonies containing Tn5-132 transpositions were isolated at a frequency of about $10^{-8}$. Tc$^R$ strains were scored for the lamB phenotypes by cross-streaking against $\lambda$ c1857 on either R+maltose (RM) or R+glucose (RG) at 42°. Wild type lamB+ strains are lambda sensitive ($\lambda^S$) on RM, but ($\lambda^R$) on RG; lambda B−strains are $\lambda^R$ on both media. The desired strain, ECG16 was $\lambda^S$ on both RG and RM; thus it is constitutive for lamB. A derivative of ECG16 designated ECG10 was isolated by maintenance under kanamycin selection, was stably Km$^R$ without selection, and remained constitutive with respect to lamB. Constitutive lambda phage adsorption in the presence of both maltose and glucose. The level of lamB production was established at approximately 1/10 that of the maltose induced lamB+ strain.

Genomic DNA was isolated from ECG10, and treated with BglII. The digest was ligated with BamHI digested pLAFRB, derived from pLAFRI (Friedman, A. M., et al, *Gene* (1982) 18:289) which is a broad host range, restricted copy number cosmid. The resulting genomic library in pLAFRB was used to transform lamB− strain ECG17, a non-reverting $\lambda^R$ derivative of ECG10 that exhibited no residual lambda adsorption when tested by cosmid transduction. ECG17 was obtained by selecting $\lambda^R$, Mal+ derivatives of ECG10. Successful transformants were identified by tetracycline resistance, carried by the pLAFRB vector.

The successful transformants were then infected with a cosmid transducing lysate of cosmid pS11, containing unspecified Rhizobium sp. ORS571 insert DNA, which confers ampicillin resistance and is compatible with pLAFRB. The successful Amp$^R$ transductants were screened for lambda sensitivity independent of maltose and glucose levels. Plasmids were isolated from candidate strains, and screened for their ability to again transform ECG17 to tetracycline resistance. One candidate plasmid, pTROY9 conferred tetracycline resistance and carried the lamB constituitive gene as evidenced by a lambda cross-streaking test.

Upon characterization, pTROY9 was shown to carry a 7.5 kb BglII fragment with restriction sites similar to those reported for malK-lamB, the native sequence in which the lamB is found. pTROY9 had 1.3 kb more DNA in the BglII insert than is present in wild type HB101; this additional DNA carried two HindIII sites and one Pvu site. The position of these sites and the size of the additional DNA suggested that an IS3 insertion was present in the relevant portion of pTROY9. IS3 is known to be a "jumping gene" which contains suitable promoter for expression in *E. coli* (Charlier, D., et al *Nucleic Acids Res* (1982) 10:5935). This was confirmed by restriction analysis, and is consistent with the observed activity as IS3 is known to be a weak promoter for expression of distal genes.

D.3. Transfer to Other Bacteria

Because pLAFRB contains the origin of transfer (oriT) it transfers efficiently during conjugation between gram negative bacteria when a compatible, transfer-proficient (Tra+) plasmid, e.g., pRK2013 (Ditta, G., et al, *Proc Natl Acad Sci (USA)* (1980) 77:7347) is present. These two factors in combination permit the transfer of DNA cosequential with the oriT during conjugation between receptive hosts.

During conjugations, pTROY9 was transferred to *Salmonella typhimurium* and *Klebsiella pneumoniae*. Transformants were tested for lamB expression using 1) a lambda plaque assay: strains with and without pTROY plasmids were assessed for the ability to propagate lambda C1857; 2) lambda::Tn5 Transposition assay: strains were tested for the ability to rescue the $Km^R$ allele of Tn5 from lambda::Tn5 phage and 3) $\lambda^d$ (pS11) cosmid transduction assay: strains were infected by a cosmid transducing lysate and selected for the acquisition of $Amp^R$ cosmid pS11.

Both bacteria containing pTROY9 acquired the ability to be infected by λcI857 (although only *K. pneumoniae* was able to propagate λcI857), were kanamycin resistant, and were ampicillin resistant.

D.4. Construction of pTROY9' Adapted to Agrobacterium and Rhizobium

*Rhizobium meliloti* and *Agrobacterium tumefaciens* strains were allowed to conjugate with a mobilizing, transfer-proficient (TRA+) *E. coli* donor strain (Rec+) carrying both pTROY9 and pKBZ42-12. LacZ+ recipients were selected by ability to utilize lactobionic acid as sole carbon source. Because only pTROY9, and not pKBZ42-12, can replicate in these recipient organisms, derivatives that become LacZ+ by virtue of acquisition of the *E. coli* lacZ gene (from pKBZ42-12) must do so by recombination (in *E. coli* prior to DNA transfer) between homologous lamB sequences. This single recombination yields a complete cointegrate of the composite plasmid that is stable in the recipient cells as long as the appropriate selection is maintained. Such a recombination event to yield a plasmid cointegrate produces a lamB::lacZ fusion gene behind the IS3 promoter. The existence of such a cointegrate, e.g., *R. meliloti* 102F51/pTROY2041 can be demonstrated. However the IS3 promoter on pTROY9 does not direct the expression (transcription) of the lamB gene when this plasmid is transferred to *R. meliloti* or *A. tumefaciens* strains. Therefore the creation (by recombination) of a lamB::lacZ gene fusion behind the IS3 promoter is not sufficient to allow the cointegrate to confer a LacZ+ phenotype—an additional mutational event proximal to the lamB::lacZ gene fusion must occur to render the fused gene expressible in the particular recipient cell. This technique (a) allows the appropriate promoter to be created in the recipient organisms by mutation of the IS3 progenitor promoter, and (b) facilitates the selection of a functional lamB::lacZ gene fusion so created. *R. meliloti* and *A. tumefaciens* Lac+ strains, verified to contain a cointegrate plasmid, e.g., pTROY2041, are then plated on rich medium containing glucose as added carbon source and the chromogenic β-galactosidase substrate X-Gal. Because the Lac+ selection is removed and because the cointegrate plasmid contains duplication of lamB DNA sequences, the cointegrate dissociates by recombination back into component plasmids pTROY9' and pKBZ42-12, which is lost by segregation. The pTROY9' plasmids so yielded exhibit a reconstructed lamB gene that is transcribed by a promoter functional in the host strain. This promoter was created while the plasmid existed as a cointegrate. *R. meliloti* and *A. tumefaciens* strains carrying pTROY9' plasmids, e.g., pTROY9101, 9103, 9106, 9107, and 9151, allow efficient lambda infection as measured by the assays previously described (¶D.3). pTROY9151 was designated the pTROY9' adapted to *Rhizobium meliloti* and deposited with ATCC as set forth below.

On Oct. 2, 1984, Applicants have deposited with the American Type Culture Collection, Rockville, Md., USA (ATCC) pTROY9 in the host *E. coli* ECG18, ATCC accession no. 39889. On Nov. 13, 1984 Applicants deposited pTROY9' in *Rhizobium meliloti* (pTROY9151) this pTROY9' being adapted thereto as herein described, ATCC accession no. 39921. These deposits were made under the provisions of the Budapest Treaty on the International Recognition of the Deposit of Microorganisms for the Purposes of Patent Procedure and the Regulations thereunder (Budapest Treaty). This assures maintenance of a viable culture for 30 years from date of deposit. The organism will be made available by ATCC under the terms of the Budapest Treaty, and subject to an agreement between Applicants and ATCC which assures unrestricted availability upon issuance of the pertinent US patent. Availability of a deposited strain is not to be construed as a license to practice the invention in contravention of the rights granted under the authority of any government in accordance with its patent laws.

We claim:

1. A recombinant DNA sequence which comprises the DNA sequence encoding lamB protein under control of a constitutive promoter.

2. The DNA sequence of claim 1 wherein the promoter is a promoter operable in coliform hosts.

3. The DNA sequence of claim 2 which further contains a broad host range origin of replication.

4. A method to prepare a mutant strain, wherein the gene encoding lamB under control of a constitutive *E. coli* promoter which method comprises:
   (a) selecting a mutant strain of *E. coli* which is resistant to lambda phage;
   (b) selecting a revertant of the mutant strain of (a) which is sensitive to lambda infection; and
   (c) confirming the constitutive production of lamB in said revertant strain by confirming lambda sensitivity on maltose-free medium.

5. The method of claim 4 wherein the lambda resistant *E. coli* mutant is mutant in the malT protein that induces lamB promoter.

6. The method of claim 4 wherein the selection of a revertant in step (b) is conducted by employing a lambda phage carrying a marker gene.

7. The method of claim 6 wherein the marker encodes antibiotic resistance.

8. An *E. coli* strain containing lamB under control of a constitutive promoter prepared by the process of claim 4.

9. The DNA sequence of claim 3 which is pTROY9.

10. A method to obtain a DNA sequence capable of constitutive expression of lamB in a non-coliform procaryotic host which comprises:
- (a) selecting constitutive lamB producing *E. coli* cells;
- (b) excising the lamB expression system by digesting the genomic DNA of the selected cells with one or a plurality of restriction endonuclease (s);
- (c) cloning the DNA digest from (b) into a broad host range vector to obtain a precursor plasmid;
- (d) cotransforming a target procaryotic host cell with the precursor plasmid of (c) and an additional narrow host range vector containing a sequence encoding a selectable marker in the target host which sequence is ligated to DNA homologous to lamB;
- (e) selecting transformants for the selectable marker;
- (f) removing the selective pressure, and screening for loss of the selectable marker; and
- (g) recovering said lamB expression system DNA sequence.

11. A method to prepare a non-coliform procaryotic host capable of lamB expression, which method comprises:

cotransforming non-coliform procaryotic cells with
a first plasmid containing the lamB gene under control of a constitutive promoter and a broad host range origin of replication, and
a second plasmid containing a sequence encoding a selectable marker in the target host which sequence is ligated to DNA homologous to lamB;

selecting the cotransformed cells for recombination between said first and second plasmids under selection pressure for the marker; and removing the selection pressure to obtain a non-coliform procaryotic colony harboring an operable expression system for lamB.

12. The method of claim 11 which further includes recovering the lamB expression system DNA sequence.

13. The method of claim 11 wherein the plasmid containing the lamB gene under control of a constitutive promoter and a broad host range origin of replication is pTROY9.

14. The method of claim 11 wherein the marker selectable in non-coliform cells is lacZ.

15. The method of claim 11 wherein the non-coliform host cell is selected from *Agrobacterium* and *Rhizobium*.

16. Non-coliform procarzone cells prepared by the method of claim 11, wherein said cells are susceptible to lambda phage.

17. A lamB expression system DNA sequence prepared by the method of claim 10.

18. The lamB expression system DNA sequence of claim 17 which is pTROY9151.

* * * * *